US010851043B1

United States Patent
Abdulhameed et al.

(10) Patent No.: US 10,851,043 B1
(45) Date of Patent: Dec. 1, 2020

(54) COMPOUND FOR FATTY ACID SYNTHASE INHIBITION

(71) Applicant: KANNUR UNIVERSITY, Kerala (IN)

(72) Inventors: Sabu Abdulhameed, Kannur (IN); Madathilkovilakath Haridas, Kannur (IN); Prasanth Shankar, Kannur (IN)

(73) Assignee: KANNUR UNIVERSITY, Kannur (IN)

( * ) Notice: Subject to any disclaimer, the term of this patent is extended or adjusted under 35 U.S.C. 154(b) by 0 days.

(21) Appl. No.: 16/811,217

(22) Filed: Mar. 6, 2020

(30) Foreign Application Priority Data

Jul. 4, 2019 (IN) .............................. 201941026900

(51) Int. Cl.
C07C 225/14 (2006.01)
C12P 7/28 (2006.01)

(52) U.S. Cl.
CPC .............. *C07C 225/14* (2013.01); *C12P 7/28* (2013.01)

(58) Field of Classification Search
CPC .................................................. C07C 225/14
See application file for complete search history.

(56) References Cited

PUBLICATIONS

Ahmad et al. "Partial Characterization of Fatty Acid Synthase of Propionibacterium shermanii" Journal of General Microbiology (1981) 127, 121-129.
Dixit et al. "Cyanobacteria: potential candidates for drug discovery" Antonie van Leeuwenhoek; 103, pp. 947-961; Mar. 27, 2013.
Dutler et al. "Fatty Acid Synthetase from Pig Liver" Eur. J. Biochem. 22 (1971) 213-217.
Trajtenberg et al. "Structural insights into bacterial resistance to cerulenin" FEBS Journal, May 2014; 281(10):2324-38.
Filimonov et al. "The Method of Self-Consistent Regression for the Quantitative Analysis of Relationships Between Structure and Properties of Chemicals" Pharmaceutical Chemistry Journal vol. 38, pp. 21-24; Jan. 2004.
Friesner et al. "Extra Precision Glide: Docking and Scoring Incorporating a Model of Hydrophobic Enclosure for Protein-Ligand Complexes" J Med Chem. 49(21):6177-96. Oct. 19, 2006.
Friesner et al. "Supporting Information: Extra Precision Glide: Docking and Scoring Incorporating a Model of Hydrophobic Enclosure for Protein-Ligand Complexes" Oct. 19, 2006.
Li et al. "Fatty Acid Synthase Inhibitors from Plants: Isolation, Structure Elucidation, and SAR Studies" J. Nat. Prod. 65, 12, 1909-1914; Nov. 8, 2002.
Olsen et al. "Structures of β-Ketoacyl-Acyl Carrier Protein Synthase I Complexed with Fatty Acids Elucidate its Catalytic Machinery" Structure, vol. 9, issue 3, Mar. 2001, pp. 233-243.
Pappenberger et al. "Structure of the Human Fatty Acid Synthase KS-MAT Didomain as a Framework for Inhibitor Design" J. Mol. Biol. 397, 508-519; Mar. 26, 2010.
Arung et al. "Anti-Cancer Properties of Diethylether Extract of Wood from Sukun (*Artocarpus altilis*) in Human Breast Cancer (T47D) Cells" Tropical Journal of Pharmaceutical Research, Aug. 2009; 8 (4): 317-324.
P. von Wettstein-Knowles et al. "Fatty acid synthesis—Role of active site histidines and lysine in Cys-His-His-type b-ketoacyl-acyl carrier protein synthases" FEBS Journal 273 (Feb. 2006) 695-710.

Primary Examiner — Sikarl A Witherspoon
(74) Attorney, Agent, or Firm — Maschoff Brennan

(57) ABSTRACT

Fatty acids play very important and diverse roles in living organisms, from signal transduction, energy management, maintaining of structural integrity to the normal metabolic processes. Due to its diverse presence and roles, Fatty Acid Synthase (FAS) is an attractive drug target under different pathologic contexts such as cancer, TB, obesity, microbial infection, etc. There are a number of molecules targeting Fatty Acid Synthase (FAS) in the prior art like Cerulenin, Orlistat, Pyrimidine, Triclosan, C75 etc. The present invention relates to a compound of formula I having fatty acid synthase inhibitory properties which was confirmed by an FAS inhibition assay. The present invention also relates to a process for collection, extraction, isolation, purification and characterization of the claimed compound from marine cyanobacterium, *Phormidium ambiguum*.

Formula I

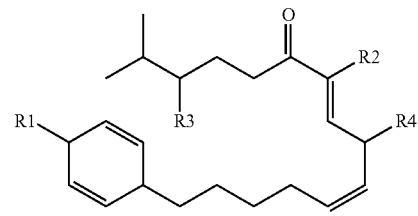

10 Claims, 8 Drawing Sheets

COMPOUND FOR FATTY ACID SYNTHASE INHIBITION

FIELD OF THE INVENTION

The present invention relates to fatty acid synthase inhibiting compounds, process of preparing the compounds, a composition containing said compounds, and use thereof for Fatty Acid Synthase inhibition.

BACKGROUND OF THE INVENTION

Fatty acids play very important and diverse roles in living organisms, from signal transduction, energy management, maintaining of structural integrity to the normal metabolic processes, etc. Due to its diverse presence and role Fatty Acid Synthase (FAS) is an attractive drug target under different pathologic contexts such as cancer, TB, obesity, microbial infection, etc. There are a number of molecules targeting Fatty Acid Synthase (FAS) in the prior art like Cerulenin, Orlistat, Pyrimidine, Triclosan, C75 etc. Different FAS targeting molecules operate through different mode of action, as these molecules bind to different components of FAS complex. But, due to drawbacks associated with use of FAS targeting molecules like side effects and varying extent of activity, there exists an ever increasing demand for novel molecules with better activity and reduced side effects.

Present invention involves methods for harvesting the source material and isolating a new molecule, from marine cyanobacterium, *Phormidium ambiguum*, which has a higher inhibitory activity than the current therapeutic drugs of the category against FAS under laboratory test conditions. Also, the newly developed process for sourcing and processing of the raw material, isolation, purification and characterization of the new molecule reduces the time and resources required otherwise when we follow conventional column chromatographic procedures. This molecule can act as a drug lead compound for the design and development of a better drug to inhibit FAS thus paving way for effective treatment against diseases like cancer, obesity and tuberculosis.

Dixit et al. (2013) focuses on anti-cancerous, antiviral and antibacterial compounds from cyanobacteria; their clinical status; extraction and detection techniques for the isolation of novel biomolecules from cyanobacteria. Marine microbial sources have become one of the major focuses of research for identifying new chemical entities with diverse biological activities. Cyanobacteria are one of the major classes among them and are known for their huge repertoire of metabolites and genetic flexibility. They are known to produce molecules with diverse pharmacological properties, such as anti-helminthic, immunosuppressant, anti-inflammatory, anti-microbial, anti-cancer, anti-coagulant activities etc.

Dutler et al. (1971) provides experimental evidence and theoretical considerations which show that the pure enzyme with oxidoreductase activity for alicyclic ketones which was isolated from pig liver is a fatty acid synthetase. The enzyme exhibits fatty acid synthetase activity with the natural substrates, acetyl- and malonyl-CoA, and when incubated with 14C-labeled acetyl-CoA, yields [$^{14}$C]-palmitate and [$^{14}$C] stearate. The oxidoreductase activity for alicyclic ketones and the fatty acid synthetase activity of the enzyme could not be separated by chromatography on two different column materials. Kinetic data obtained with the model substrate, S-acetoacetyl-N-acetylcysteamine, as well as stereospecificity considerations support the view that it is the 3-oxoacylacyl-carrier protein reductase component of the fatty acid synthetase complex, which is responsible for the oxidoreductase activity toward alicyclic ketones.

Li et al. (2002) discloses Fatty acid synthase (FAS) inhibitors as potential anti-fungal agents. FAS prepared from *Saccharomyces cerevisiae* was employed for bioactivity-guided fractionation of *Chlorophora tinctoria, Paspalum conjugatum, Symphonia globulifera, Buchenavia parviflora*, and *Miconia pilgeriana*. Thirteen compounds including three new natural products were isolated and their structures identified by spectroscopic interpretation. They represented five chemotypes, namely, isoflavones, flavones, biflavonoids, hydrolyzable tannin-related derivatives, and triterpenoids. 3'-Formylgenistein (1) and ellagic acid 4-O-alpha-1-rhamnopyranoside (9) were the most potent compounds against FAS, with IC$_{50}$ values of 2.3 and 7.5 microgram/mL, respectively. Structure-activity relationships for some chemotypes were investigated. All these compounds were evaluated further for antifungal activity against *Candida albicans* and *Cryptococcus neoformans*.

Therefore, in view of the above there is an unmet need for an FAS inhibitor with better activity and lesser side effects compared to the inhibitors already known in the art. The known processes for preparing FAS inhibitors suffer from problems, such as a cumbersome purification of the product by column chromatography, low yields, use of costly, hazardous, environmentally unsafe, carcinogenic or pyrophoric reagents, etc. on industrial scale. There is a need for simple, industrially scalable, cost effective and environment-friendly processes for the preparation of FAS inhibitors that is free from above mentioned drawbacks and achieves high yield and purity. Isolation, purification and characterization of the new molecule using a combined solvent extraction and precipitation method by exploiting the change in polarity of the solvent system make the process unique. Unlike purification by conventional column chromatography, this method reduces cost of solvents and time.

SUMMARY OF THE INVENTION

In an embodiment, the present invention provides a compound of general Formula I:

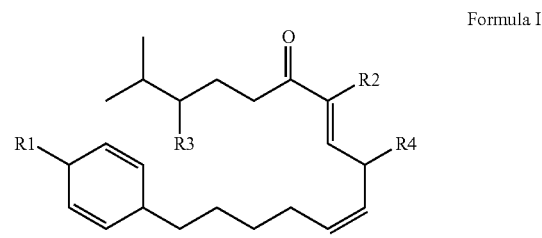

Formula I or a salt, ester, prodrug or isomers thereof, wherein R1, R2 and R3 are independently selected from the group consisting of alkyl halides; halide esters; allylation reaction products of primary, secondary, tertiary and higher alcohols including benzylic, propargylic, allylic, and other aliphatic alcohols; nucleophilic substitution products of the hydroxyl group in stereogenic alcohols; stereospecific-nucleophilic-substitution-of-hydroxyl groups; electrophilic aromatic substitution products of oxygen of hydroxyl groups formed by aromatic nitration, aromatic halogenation, aromatic sulfonation, and acylation and alkylating reaction to yield products such as alkyl/aryl halides; products formed by ester formation with electrophilic derivatives of carboxylic and sulfonic acids; amides and R4 is —NH₂.

In a preferred embodiment, the compound is represented by (3S,5Z,7S,8Z)-7-amino-3,5-dihydroxy-2-methyl-13-[(1s,4s)-4-hydroxycyclohexa-2,5-dien-1-yl]trideca-5,8-dien-4-one (Formula II):

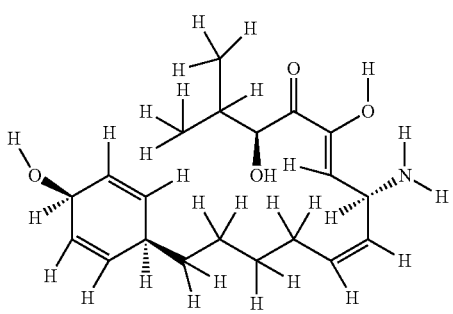

Formula II

In another embodiment, the present invention provides a compound of Formula I having anti-tumor activity.

In another embodiment, the present invention provides a compound of Formula I having anti-proliferative activity.

In another embodiment, the present invention provides a compound of Formula II exhibiting in-vitro anti-proliferative activity against A549 lung carcinoma cells with $IC_{50}$ of 74-78 μg/mL.

In another embodiment, the present invention provides a compound of Formula II exhibiting in-vitro anti-proliferative activity against A549 lung carcinoma cells with $IC_{50}$ of 76.034 μg/mL.

In another embodiment, the present invention provides a compound of Formula I having fatty acid synthase inhibition activity.

In another embodiment, the present invention provides a compound of Formula II having a $^1H$ and $^{13}C$ NMR spectra with signals at δH 7.26 correlated with δC 67.62; δR at 2.46 to 2.62 and δC at 29.64; δH at 1.25 to 1.67; and 5.23 to 5.27.

In a further embodiment, the present invention provides a process for preparing the compound of the Formula I.

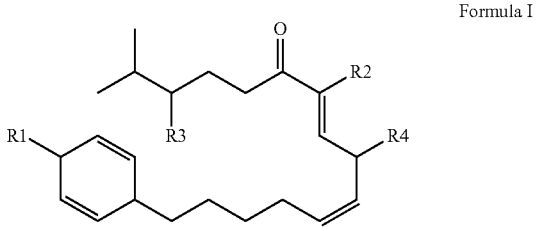

Formula I or a salt, ester, prodrug, a pharmaceutically acceptable salt or individual optical isomers thereof; wherein R1, R2 and R3 are independently selected from the group consisting of alkyl halides; halide esters;

allylation reaction products of primary, secondary, tertiary and higher alcohols including benzylic, propargylic, allylic, and other aliphatic alcohols; nucleophilic substitution products of the hydroxyl group in stereogenic alcohols; stereo-specific-nucleophilic-substitution-of-hydroxyl groups; electrophilic aromatic substitution products of oxygen of hydroxyl groups formed by aromatic nitration, aromatic halogenation, aromatic sulfonation, and acylation and alkylating reaction to yield products such as alkyl/aryl halides; products formed by ester formation with electrophilic derivatives of carboxylic and sulfonic acids; amides, and R4 is —NH₂ and comprising the steps of:

a. collecting cyanobacterial biomass by scrapping off the cyanobacteria from semi submerged rock pits and washing with water;
b. squeezing and grinding the biomass with ethanol to obtain a fine paste of the biomass;
c. drying and solidifying the paste obtained in step (b);
d. grinding the solidified paste obtained in step (c) in to a powder;
e. defatting the biomass powder obtained in step (d);
f. extracting the defatted powder obtained in step (e) using soxhlet to obtain a pale white precipitate;
g. concentrating the extract obtained in step (f) to ⅕$^{th}$ the volume;
h. precipitating the concentrated extract obtained in step (g) using methanol and re-dissolving in chloroform;
i. repeating step (h) 3 to 4 times or until precipitate of pale white color are obtained;
j. purifying the precipitate obtained in step (i) using column chromatography;
k. purifying the compound obtained in step (j) using vacuum liquid chromatography; and
l. purifying the compound obtained in step (k) using reverse phase High Pressure Liquid Chromatographic (R-HPLC).

In yet another embodiment, the invention provides a process for preparing the compounds of Formula I using cyanobacterial biomass is collected during the period of January to May.

In yet another embodiment, the invention provides a process for preparing the compounds of Formula I, wherein the drying and solidifying is carried out by spreading a thin layer of the paste.

In yet another embodiment, the invention provides a process for preparing the compounds of Formula I, wherein the collected cyanobacterial biomass is processed within 1-2 hours to avoid microbial degradation.

In another embodiment, the invention provides a process for preparing the compounds of Formula I, wherein the defatting is carried out using hexane.

In yet another embodiment, the invention provides a process for preparing the compounds of Formula I, wherein the extraction of defatted powder is carried out at 60° C. to 70° C.

In yet another embodiment, the invention provides a process for preparing the compounds of Formula I, wherein the extraction of defatted powder is carried out at 65° C.

In yet another embodiment, the invention provides a process for preparing the compounds of Formula I, wherein extraction of defatted powder is carried out for 6 to 8 hours.

In yet another embodiment, the invention provides a process for preparing the compounds of Formula I, wherein the extraction of defatted powder is carried out using chloroform.

In yet another embodiment, the invention provides a process for preparing the compounds of Formula I, wherein the concentration of extract is carried out using a rotary vacuum evaporator operated at 145-155 rpm/and at 35-45° C.

In yet another embodiment, the invention provides a process for preparing the compounds of Formula I, wherein the concentration of extract in step (g) is carried out using a rotary vacuum evaporator operated at 150 rpm at 40° C.

In yet another embodiment, the invention provides a process for preparing the compounds of Formula I, wherein the column chromatography is silica gel chromatography and is carried out using ethyl acetate, dichloromethane and methanol as solvents for gradient elution.

In yet another embodiment, the invention provides a process for preparing the compounds of Formula I, wherein the elution for the purification step in column chromatography is initiated with 100% ethyl acetate followed by attaining 100% dichloromethane in the middle and finally using 100% methanol in the stage.

In yet another embodiment, the invention provides a process for preparing the compounds of Formula I, wherein the vacuum liquid chromatography uses 100% dichloromethane to 100% methanol for elution.

In yet another embodiment, the invention provides a process for preparing the compounds of Formula I, wherein the reverse phase High Pressure Liquid Chromatographic (R-HPLC) uses a gradient elution with acetonitrile to water at a constant flow rate of 0.2 mL/min with a constant column temperature of 30° C.

In yet another embodiment, the invention provides a process for preparing the compound of Formula II.

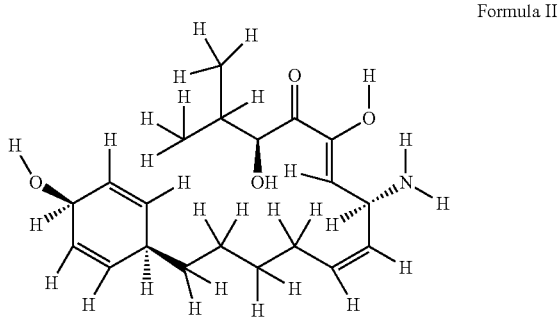
Formula II

In yet another embodiment, the present invention relates to a pharmaceutical composition comprising compound of Formula I or II and produced by process as described above, along with the pharmaceutically acceptable excipients, diluents, additives.

In yet another embodiment, the present invention relates to a pharmaceutical composition used for fatty acid synthase inhibition.

Further embodiments, features, and advantages of the present invention, as well as the structure and operation of the various embodiments of the present invention, are described in detail below with a reference to the accompanying drawings.

OBJECT OF THE INVENTION

An object of the present invention is to provide a process for collection of source material, extraction and purification of the compound having Fatty Acid Synthase (FAS) inhibitory properties.

Another object of the present invention is to prepare a compound which shows Fatty Acid Synthase (FAS) inhibitory properties.

Another object of the present invention is to provide a compound which shows increased interaction with FAS I and FAS II enzymes compared to other inhibitors known in the domain, thus showing increased inhibition compared to the known inhibitors.

DETAILED DESCRIPTION OF THE INVENTION

Figure 1:
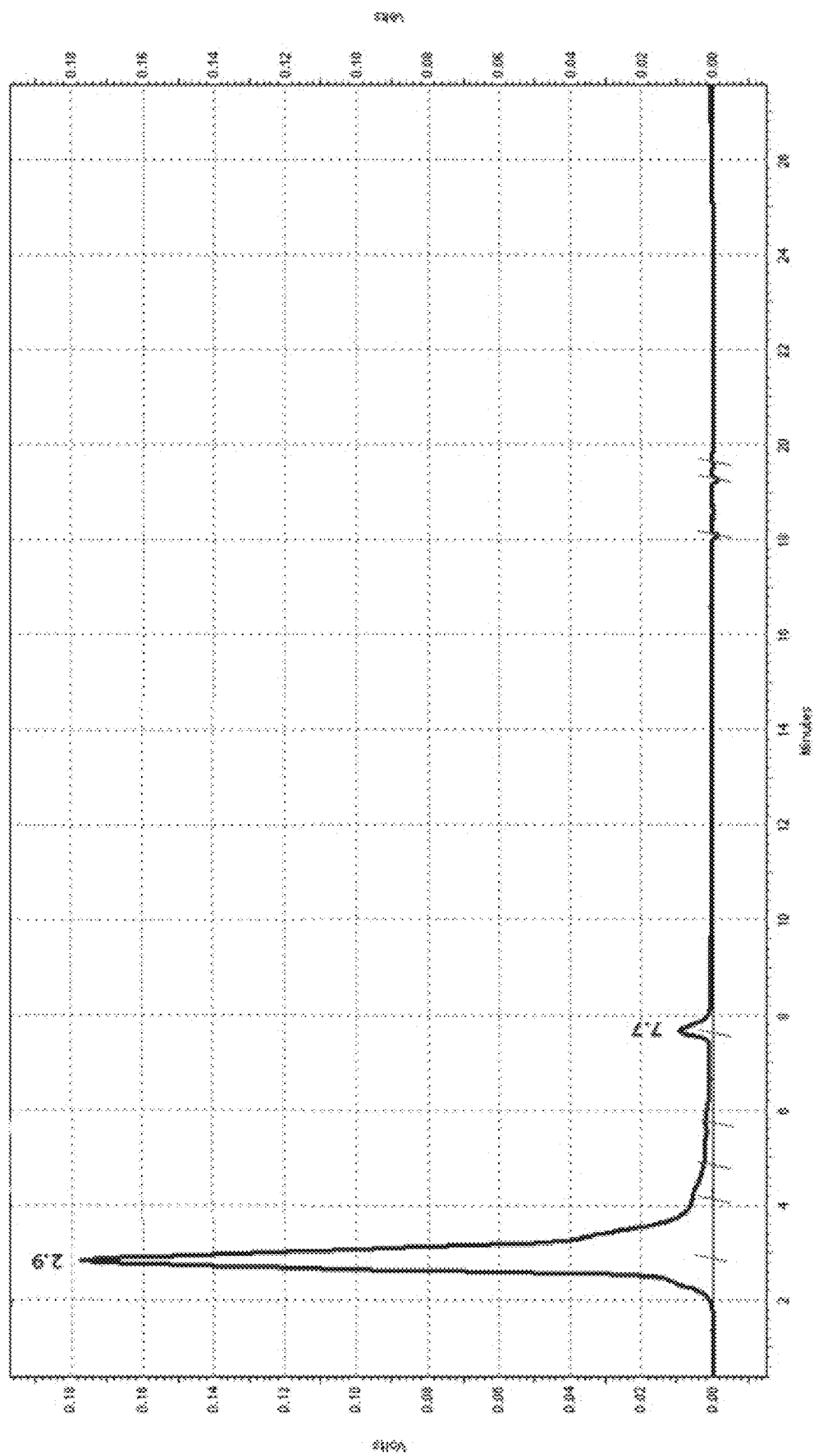
FIG. 1 illustrates preparative HPLC profile of purified compound of Formula II

While the invention is susceptible to various modifications and alternative forms, specific embodiments thereof is described in detail in examples section below. It should be understood, however that it is not intended to limit the invention to the particular forms disclosed, but on the contrary, the invention is to cover all modifications, equivalents, and alternative falling within the scope of the invention as defined by the appended claims.

The present invention relates to a general compound of Formula I.

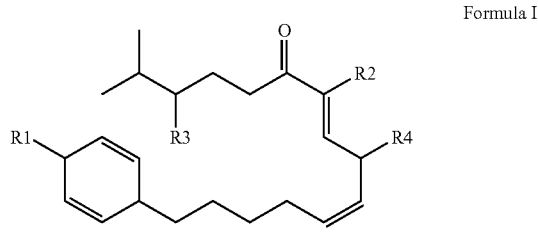
Formula I wherein R1, R2 and R3 are independently selected from the group consisting of alkyl halides; halide esters; allylation reaction products of primary, secondary, tertiary and higher alcohols including benzylic, propargylic, allylic, and other aliphatic alcohols; nucleophilic substitution products of the hydroxyl group in stereogenic alcohols; stereospecific-nucleophilic-substitution-of-hydroxyl groups; electrophilic aromatic substitution products of oxygen of hydroxyl groups formed by aromatic nitration, aromatic halogenation, aromatic sulfonation, and acylation and alkylating reaction to yield products such as alkyl/aryl halides; products formed by ester formation with electrophilic derivatives of carboxylic and sulfonic acids; amides and R4 is —NH$_2$.

The present invention relates to a specific compound, (3S,5Z,7S,8Z)-7-amino-3,5-dihydroxy-2-methyl-13-[1s, 4s)-4-hydroxycyclohexa-2,5-dien-1-yl]trideca-5,8-dien-4-one, represented by the Formula II

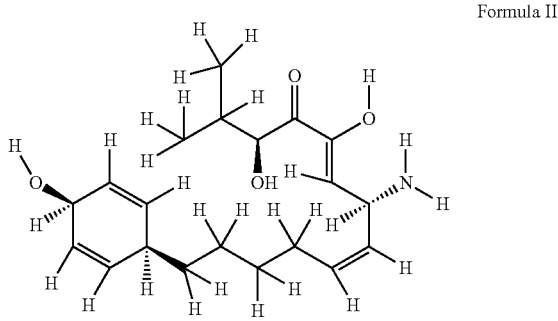

Formula II

Collection of Marine Cyanobacterium for Preparation of Extract

Cyanobacteria samples were collected during the period of January to May. Cyanobacterial cell biomass was found at semi submerged rock pits. During the high tide these pits remain submerged around a depth of about 0.5 to 1 meter but at low tide time seawater moves back and the pits become exposed. Although exposed these pits are always filled with sea water. Cyanobacterial biomass was collected from the rocks and moved to a plastic container. Collected cell biomass was worked on within 1 to 2 hours of collection to avoid microbial degradation which would affect the intended compound yield. The collected sample was then washed under tap water to remove off any sand, mud and other small sea creatures associated with the cell biomass. Then, the cleaned biomass was squeezed well to get rid of excess water and ground with a small volume of ethanol in a laboratory blender to form a fine paste. This paste was then spread as thin layer on the surface of a large glass plate and refrigerated till it dried and solidified.

Preparation of Compound

Dried cell biomass obtained was reduced to fine powder using a laboratory blender. Approximately 400-600 g of the powdered cyanobacterial cell mass was defatted with hexane. The defatted powder was then dried and subjected to Soxhlet extraction at 60° C. to 70° C. with chloroform for about 6 to 8 hrs. The chloroform extract was concentrated to $\frac{1}{5}^{th}$ the volume using a rotary vacuum evaporator at 145 rpm-155 rpm and 35° C. to 45° C. The concentrate was then added to excess of methanol in a separating funnel, stirred and kept overnight till a greenish precipitate was formed. The greenish precipitate was removed and re-dissolved in minimal amount of chloroform. This step was repeated 3 to 4 times until the precipitate turned to pale white in color.

Purification

The Pale white waxy compound obtained above was further purified using silica gel column chromatography. The column was subjected to gradient elution using ethyl acetate to methanol, and finally dichloromethane. The column was subjected to gradient elution using 100% ethyl acetate to 100% methanol with attainment of 100% dichloromethane in the middle of the chromatography. Elution was started with ethyl acetate alone and subsequently dichloromethane was added in an increments of 5 to 20% (volume/volume) thus making a total of 100% of eluent. Similarly, in the middle of the chromatographic protocol, the attained 100% dichloromethane was diluted to zero with the third solvent methanol which was added in increments of 10% in volume/volume yielding 100% methanol at the end. Elution and fraction collected was not based on time interval but on volume basis. The compound was eluted at dichloromethane:methanol 1:1 and was precipitated out as clear white waxy form when excess methanol was added to the eluent. A second purification step was carried out using vacuum liquid chromatography with TLC grade silica. Elution was carried out with dichloromethane to methanol gradient and the compound was eluted at a ratio of dichloromethane:methanol 1:1. Final purification was carried out using reverse phase High Pressure Liquid Chromatographic (R-HPLC). Gradient elution was performed with acetonitrile to water at a constant flow rate of 0.2 mL/min with a constant column temperature of 30° C. The compound finally eluted exhibits a retention time (RT) of 2.9 in preparative HPLC under the said conditions (FIG. 1). The HPLC column was eluted with the acetonitrile:water ratio in such a way that initially the eluent was at 100% acetonitrile, with an increase in gradient of water, such that column was eluted with 100% water by the end of 30 minutes.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Example 1

Preparation of Compound of Formula II

Cyanobacteria samples were collected during the period of January to May from Ezhara beach (GPS coordinates 11° 49'09.9"N 75° 25'02.9"E), Kannur district, Kerala, India. Cyanobacterial biomass was collected from submerged rock pits by scrapping off the cyanobacteria using a metal chisel with wide end to detach the cyanobacterial cells from the rocks. The floating cell biomass from the pits was collected using a small net and moved to a plastic container. Collected cell biomass was worked on within 1 to 2 hours of collection to avoid microbial degradation which would affect the intended compound yield. If the collected biomass is used immediately for extraction, a 40% increase in yield was observed compared to delayed extraction. The collected sample was washed and then squeezed well to get rid of excess water and ground with a small volume of ethanol in a laboratory blender to form a fine paste. This paste was spread as thin layer on the surface of a large glass plate and refrigerated till it dried and solidified. Dried cell biomass obtained was reduced to a fine powder using a laboratory blender. Approximately 500 g of the powdered cyanobacterial cell mass was defatted with hexane. The defatted powder was then dried and subjected to Soxhlet extraction at 65° C. with chloroform for about 6 to 8 hrs. The chloroform extract was concentrated to ⅕th the volume using a rotary vacuum evaporator at 150 rpm/40° C. The concentrate was then added to excess of methanol in a separating funnel, stirred and kept overnight till a greenish precipitate was formed. The greenish precipitate was removed and re-dissolved in minimal amount of chloroform. This step was repeated 3 to 4 times until the precipitate turned to pale white in color. The Pale white waxy compound was further purified using silica gel column chromatography (5×30 mm column) using 240 mesh size silica. The column was subjected to gradient elution using 100% ethyl acetate to 100% methanol with attainment of 100% dichloromethane in the middle of the chromatography. Elution was started with ethyl acetate alone and subsequently dichloromethane was added in 10% increments (volume/volume) as shown in the table, thus making a total of 100 mL of eluent. Similarly, in the middle of the chromatographic protocol, the attained 100% dichloromethane was diluted to zero with the third solvent methanol which was added in increments of 10% in volume/volume yielding 100% methanol at the end (Elution and fraction collected was not based on time interval but on volume basis). The compound was eluted at dichloromethane:methanol 1:1 and was precipitated out as clear white waxy form when excess methanol was added to the eluent.

TABLE 1

Solvent gradient system for elution in silica gel chromatography

| Column loading and starting of elution | Solvent A 100% Ethyl acetate | Solvent B 0% Dichloromethane |
|---|---|---|
|  | 90% | 10% |
|  | 80% | 20% |
|  | 70% | 30% |
| ↓ | 60% | 40% |
|  | 50% | 50% |
|  | 40% | 60% |
| ↓ | 30% | 70% |
|  | 20% | 80% |
|  | 10% | 90% |
|  | 0% | 100% |
| ↓ | Dichloromethane | Methanol |
|  | 100% | 0% |
|  | 90% | 10% |
|  | 80% | 20% |
| ↓ | 70% | 30% |
|  | 60% | 40% |
| The compound was eluted at dichloromethane:methanol 1:1. | 50% | 50% |
| ↓ | 40% | 60% |
|  | 30% | 70% |
|  | 20% | 80% |
| ↓ | 10% | 90% |
|  | 0% | 100% |

A second purification step was carried out using vacuum liquid chromatography with TLC grade silica 60H (1.5×15 mm column). Elution was carried out with dichloromethane to methanol gradient and the compound was eluted at a ratio of dichloromethane:methanol 1:1.

TABLE 2

Solvent gradient system for elution in vacuum liquid chromatography

| Column loading and starting of elution | 100% Dichloromethane | 0% Methanol |
|---|---|---|
| ↓ | 90% | 10% |
|  | 80% | 20% |
|  | 70% | 30% |
| ↓ | 60% | 40% |
| Compound eluted out of the column | 50% | 50% |
|  | 40% | 60% |
|  | 30% | 70% |
|  | 20% | 80% |
|  | 10% | 90% |
| Final elution of the column | 0% | 100% |

Final purification is carried out using reverse phase High Pressure Liquid Chromatographic, R-HPLC system equipped with Extend—C18 column of 1.8 μm, 2.1×50 mm, Diode Array Detector in combination with Chem32, Chemstation software. Gradient elution was performed with acetonitrile to water at a constant flow rate of 0.2 mL/min with a constant column temperature of 30° C. The compound finally eluted exhibits a retention time (RT) of 2.9 in preparative HPLC under the said conditions (FIG. 1). The HPLC column was eluted with the acetonitrile:water ratio in such a way that initially the eluent is at 100% acetonitrile, with an increase in gradient of water, such that column is eluted with 100% water by the end of 30 minutes.

Example 2

Characterization of the Eluted Compound

Structure Elucidation

1. Fourier-Transform Infrared Spectroscopy

Figure 2:
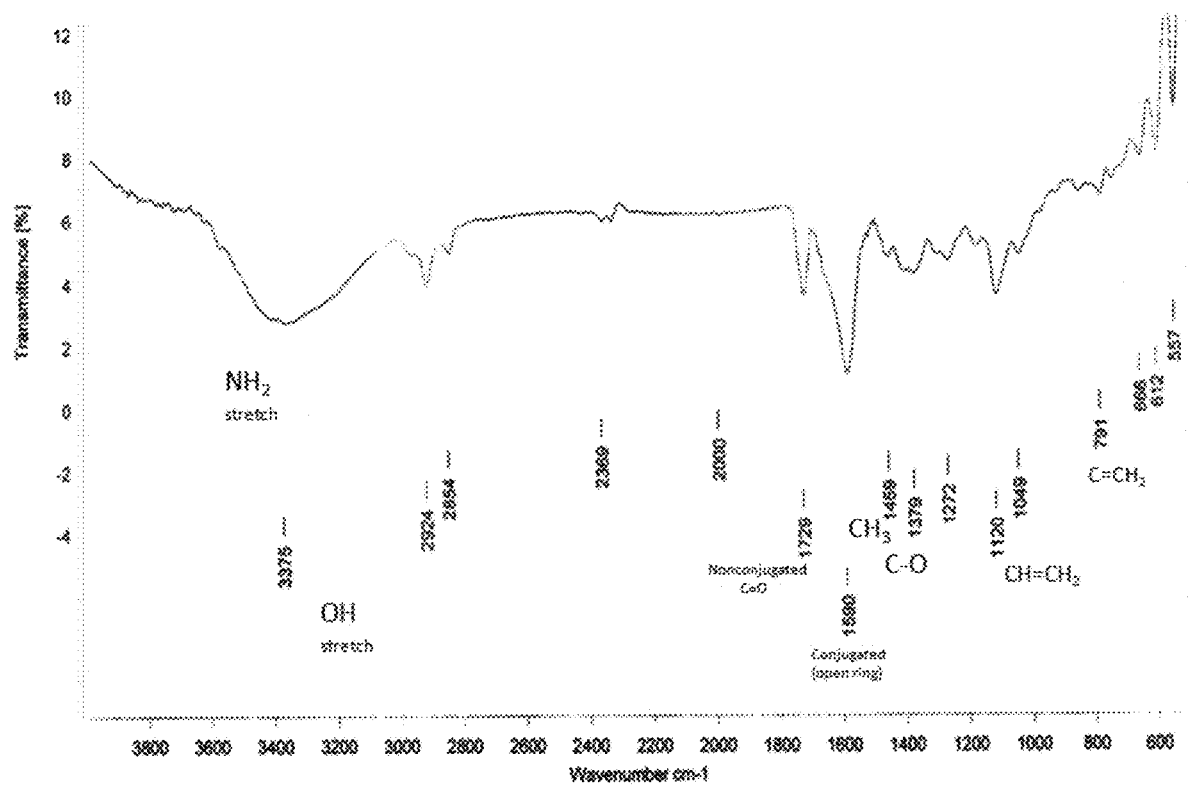
FIG. 2 illustrates FTIR Spectrum of Compound of Formula II

Infrared (IR) spectra was taken on a FTIR spectrophotometer as neat. The Fourier Transform Infrared Spectroscopy (FTIR) spectrum exhibited the presence of alkenes, alkanes, hydroxy and aldehyde groups is shown in FIG. 2.

2. Mass Spectrometry

Figure 3:
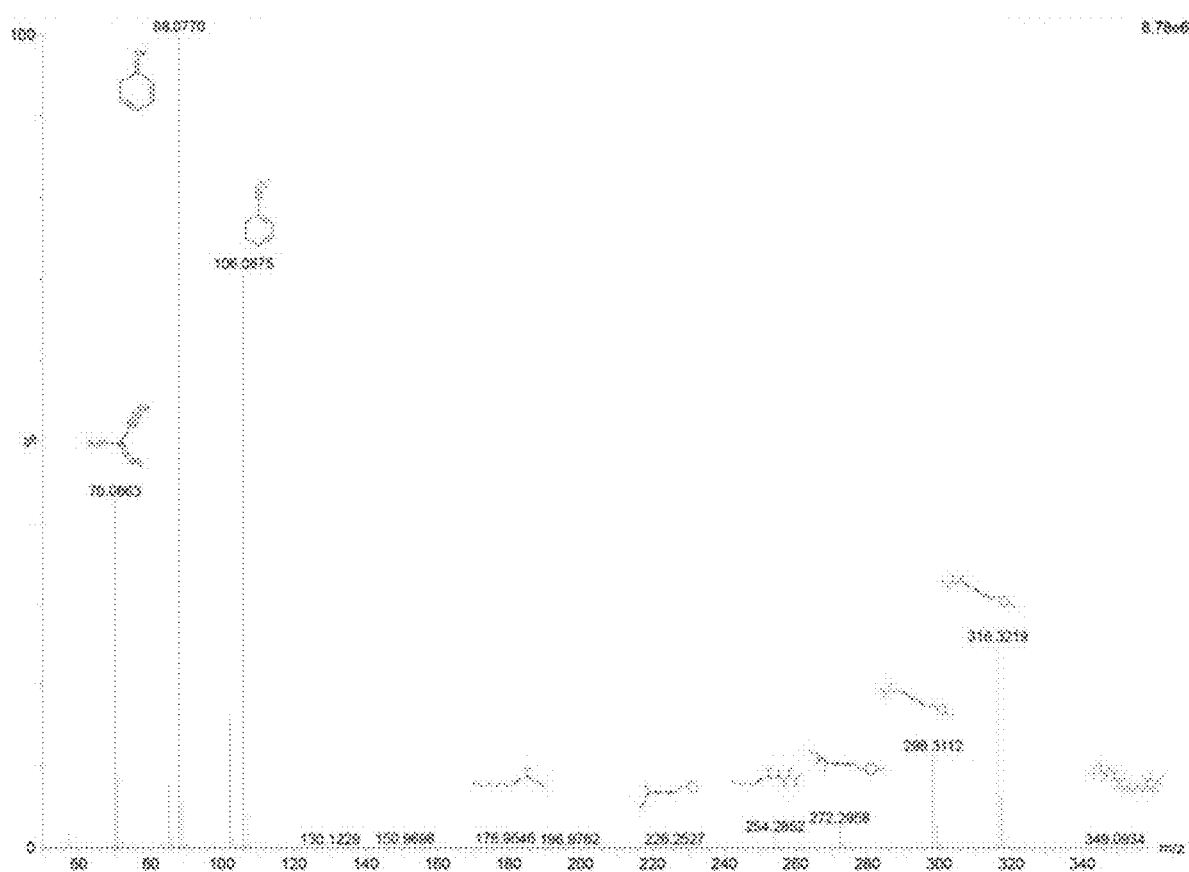
FIG. 3 illustrates LC MS/MS Spectrum of Compound of Formula II
Figure 5:
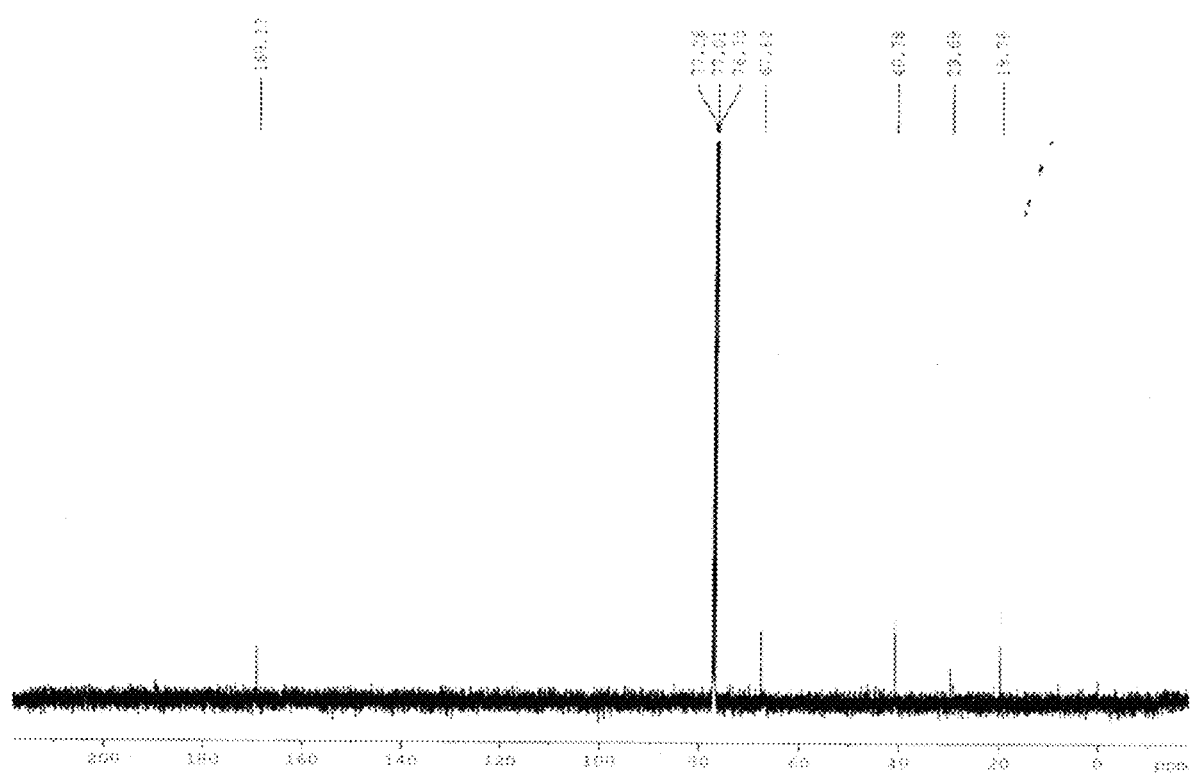
FIG. 5 illustrates $^{13}$C NMR Spectrum of Compound of Formula II

Molecular weight of the compound was determined by LCMS/MS equipped with Aquity BEH c 18 1.7 μM column having 2.1×50 mm dimensions. QTOF MS/MS data revealed m/z value of 349.093 from which its molecular Formula was determined to be $C_{20}H_{31}NO_4$. This was consistent with the molecular composition calculated by CHN analysis which gave a value of C: 0.687, H: 0.089, N: 0.040, O: 0.183. The molecular weight of the compound was later calculated to be 349.475 g/mol (FIG. 3). The fragmentation data search from LC MS/MS spectrum did not match with any compound from the database. So, NMR data was required for structure solution. The structure of the novel compound was resolved from the LC MS/MS data together with NMR spectra as below (FIG. 5).

Figure 4:
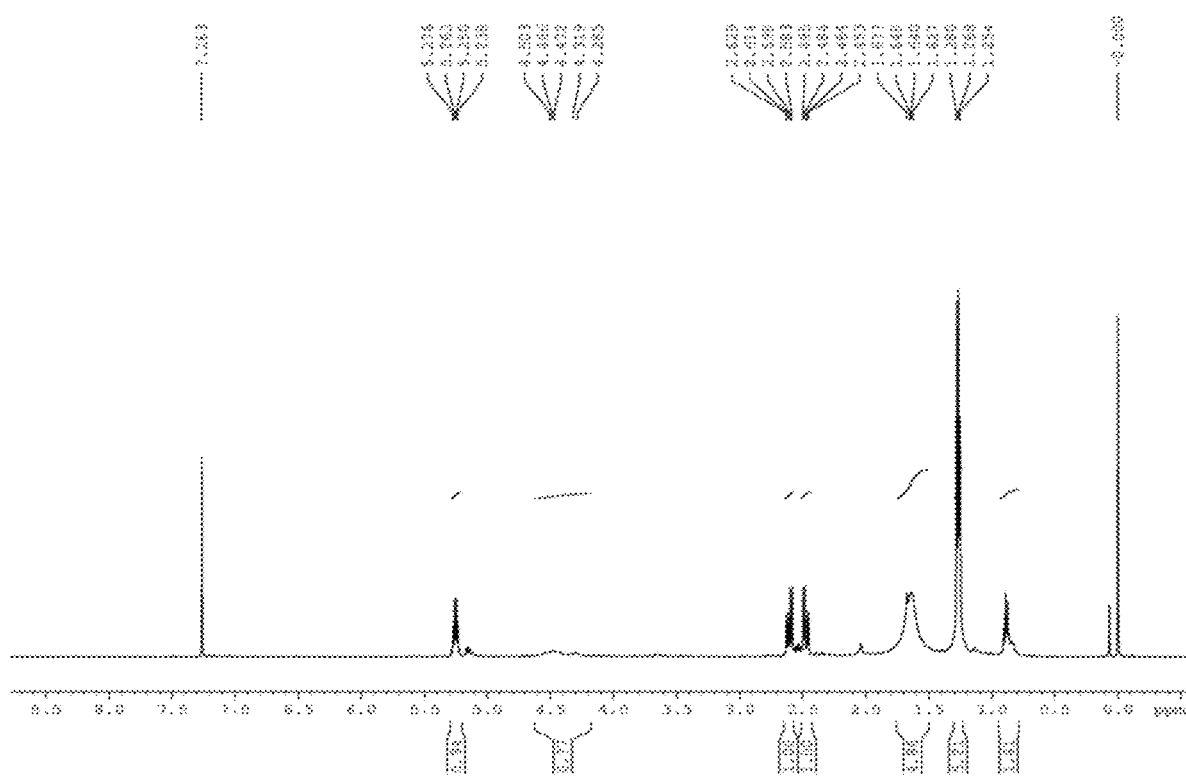
FIG. 4 illustrates $^1$H NMR Spectrum of Compound of Formula II

3. Nuclear Magnetic Resonance Spectroscopy $^1$H NMR spectra were recorded and the chemical shifts were expressed in δ (ppm) with trimethylsilane as an internal reference. $^1$H NMR and $^{13}$C NMR spectra were recorded operating at 500 MHz for $^1$H NMR and 500 MHz for $^{13}$C spectra. The chemical shifts were given in ppm (δ) and were referenced relative to CDCl3 (δ7.26 and 77.24 ppm for $^1$H and $^{13}$C NMR respectively). From the $^1$H NMR and $^{13}$C NMR spectra, the isolated compound was confirmed as (3S,5Z,7S,8Z)-7-amino-3,5-dihydroxy-2-methyl-13-[(1s,4s)-4-hydroxycyclohexa-2,5-dien-1-yl] trideca-5,8-dien-4-one as observed from FIGS. 4 and 5 respectively. The $^1$H and $^{13}$C NMR spectra pointed to a compound with long aliphatic chain and an open ring. Signals at δH 7.26 correlated with δC 67.62 suggesting the presence of an NH group. δH at 2.46 to 2.62 and δC at 29.64 pointed to the presence of $CH_2$ groups. δR at 1.25 to 1.67 was attributed to presence of $CH_3$ and 5.23 to 5.27 to $C=CH_2$ respectively. This was in correlation with δC 19.76 and confirmed the long aliphatic chain. δC at 169.17 indicated a CH=CH and an absence of any signal corresponding to aromatic ring, inferred to an open ring structure. Activity spectra of the identified compound were predicted using PASS prediction server (http://www.way2drug.com/PASSOnline/) (Filimonov et al., 2004) which generated FAS as possible lead target enzyme.

Example 3

Anti-Tumor Assay

1. Determination of In-Vitro Cytotoxic Effect on Cultured L929 Cells

Cultures of L929 (Fibroblast cells) were maintained in Dulbecco's modified eagles media supplemented with 10% fetal bovine serum (FBS) and grown to confluence at 37° C. and 5% $CO_2$ in a humidified atmosphere using a $CO_2$ incubator. The cells were trypsinised (500 µL of 0.025% Trypsin in PBS/0.5 mM Ethylene diamine tetraacetic acid (EDTA) solution for 2 minutes and passed to T flasks under complete aseptic conditions. Test compounds were added to grown cells at a final concentration of 6.25, 12.5, 25, 50 and 100 µg/mL from a stock of 1 mg/mL and incubated for 24 hours. The percentage difference in viability was determined by standard MTT assay after 24 hours of incubation. The MTT assay is a colorimetric assay for assessing cell metabolic activity. NAD (P) H-dependent cellular oxidoreductase enzymes under defined conditions, reflect the number of viable cells present.

Cytotoxicity test revealed that the compound of Formula II had an $LD_{50}$ of about 89.65 (µg/mL) against L929 cell lines. Viability percentage was calculated using the Formula, % viability=(OD of Test/OD of control)×100, where control OD was 0.993.

TABLE 3

Result of cytotoxic assay against L929 cells using compound of Formula II

| Sample Concentration (µg/mL) | Average Absorbance @ 540 nm | Percentage Viability |
|---|---|---|
| Control | 0.993 | 99.9 |
| 6.25 | 0.901 | 90.821 |
| 12.5 | 0.852 | 85.793 |
| 25 | 0.741 | 74.680 |
| 50 | 0.638 | 64.262 |
| 100 | 0.554 | 55.768 |

2. In-Vitro Anti-Proliferative Property on Cultured A549 Cells

A549 lung carcinoma cells were maintained in Dulbecco's modified eagles media (Himedia, India) supplemented with 10% FBS (Invitrogen, India) and grown to confluence at 37° C. and 5% $CO_2$ in a humidified atmosphere using a $CO_2$ incubator (NBS, Eppendorf, Germany). The cells were trypsinized (500 µL of 0.025% trypsin in PBS/0.5 mM EDTA solution (Himedia, India) for 2 minutes and transferred to T flasks under aseptic condition. Test compounds were added to grown cells with a final concentration of 6.25, 12.5, 25, 50, 100 µg/mL from a stock of 1 mg/mL and incubated for 24 hours. The % difference in viability was determined by standard MTT assay (Arung et al. 2000) after 24 hours of incubation. Viability percentage was calculated using the Formula, % viability=(OD of Test/OD of Control)×100

Compared to the LD50 of about 89.65 (µg/mL) against L929 cell lines, A549 cells showed higher susceptibility to the compound of Formula II. It means that the compound of Formula II is required in lesser amount to obtain equivalent level of cytotoxicity. In other words, A549 cells need less amount of the compound of Formula II compared to L929 cell lines to obtain complete destruction of cancer cells of type A549. This may be assumed to be still less in certain other cancer cells. In addition, it is observed that more amounts of Cerulenin and C75 are required as compared to the compound of Formula II to achieve the same level of cancer cell destruction.

TABLE 4

In-vitro anti-proliferative effect of compound of Formula II, C75 and Cerulenin on cultured A549 cells

| Sample Concentration (µg/mL) | Percentage Viability Compound of Formula II | Percentage Viability Cerulenin | Percentage Viability C75 |
|---|---|---|---|
| 6.25 | 92.302 | 100.0 | 100.0 |
| 12.5 | 89.669 | 96.869 | 100.0 |
| 25 | 67.385 | 72.007 | 80.110 |
| 50 | 55.654 | 62.247 | 66.483 |
| 100 | 42.615 | 48.066 | 55.985 |
| $IC_{50}$ µg/mL | 76.034 | 86.419 | 99.034 |

Example 4

FAS Assay

Preparation of Bacterial FAS II Enzyme for FAS Assay

Crude FAS containing protein fraction was isolated according to the modified protocol of Ahmad et al. (1981). Stock culture of *Bacillus subtilis* was inoculated in 100 mL LB broth pH 7.2 and cultured for 24 hours at room temperature. It was used for further inoculation of four 1000 mL flasks with same media and culture conditions. The flasks were placed in a rotator shaker to ensure adequate suspension of cells. Bacteria were harvested during the late-exponential phase of growth by centrifugation at 10000×g for 10 minutes and washed twice with 50 mM sodium phosphate buffer (pH 7.0) to provide cell pastes which were stored at −20° C. until use. Frozen cell pastes (25-35 g) were thawed and suspended in 50 mM sodium phosphate buffer (pH 7.0). The cell suspension was disrupted by sonication (12 W, 6×15 pulses with 15 second intervals) in 2 mL Eppendorf tubes containing 1.5 mL of cell suspension, supplemented with lysozyme (250 µg/mL) in a sonicator, operating at maximum power output while maintaining the temperature below 4° C. Unbroken cells and cell debris were removed by centrifugation at 30000×g for 30 minutes at 4° C. The pellets were re-suspended in 50 mM sodium phosphate buffer (pH 7.0) and made up to appropriate volume and subjected to ammonium sulphate precipitation. Solid ammonium sulphate was added and the protein precipitate at 40-60% saturation was collected by centrifugation, dialyzed and used for further assay.

Extraction of FAS I Enzyme from Bovine Liver

Crude preparation of FAS I enzyme was made according to modified protocol of Dulter et al. (1971). Liver from freshly slaughtered Indian water buffalo was collected and transported in ice bucket and kept at 4° C. till processing. The liver was processed at the earliest by removing connective tissues and sliced into small pieces. Using a blender, about 750 g of liver was minced to form a suspension with 0.05 M potassium phosphate buffer pH 7.4 containing 1 mM EDTA to make up to a volume of 2.5 liters. The thick solution was centrifuged at 7500×g for 20 minutes to remove meat debris and the supernatant obtained was further centrifuged at 30000×g for 30 minutes to get a translucent solution. The supernatant was further diluted to specific volume using 0.05 M Potassium phosphate buffer (pH 7.4) with 1 mM EDTA and brought initially to 10% and then to 40% saturation with solid ammonium sulfate at 4° C. The 40% ammonium sulfate fraction was centrifuged and protein precipitate was re-dissolved in 0.05 mM Tris HCl buffer, pH 7.4, dialyzed against same buffer. The FAS I enzyme was further purified by ion exchange chromatography with Diethylaminoethyl (DEAE) cellulose column as described above (Dulter et al. 1971).

FAS Assay

FAS assay for FAS I enzyme was performed according to a modified process of Li et al. 2002. Crude protein was made up to a concentration of 0.5 mg/mL of protein and used for the assay. Assay was carried out in 96 well plates with the final working volume of 100 μL. Compounds to be tested were incubated with previously made crude protein extract for 30 minutes at 25° C. 50 μL of this mixture was added to 50 of reaction mixture containing 1 mM each of malonyl CoA and Nicotinamide adenine dinucleotide phosphate (NADPH), 40 μM acetyl CoA, and 2 mM Dithiothreitol (DTT) in phosphate buffer (250 mM).

The microplate was read immediately for 10 minutes at 340 nm. FAS activity was calculated by subtracting the optical density (OD) value obtained after 1 minute from the OD value obtained after 10 minutes. FAS activity was calculated and compared with that of control and test compounds. Dimethyl sulfoxide (DMSO) was taken as control as it was used to dilute the compounds. DMSO (1%) was also tested and did not interfere with FAS activity. The negative control consisted of protein plus reaction buffer. Another control consisted of buffer reaction without protein. The $IC_{50}$ was determined by linear regression. FAS activity was determined by the rate of oxidation of NADPH to NADP which was monitored at 340 nm. The change in concentration of NADPH during oxidation was calculated using the following equation:

$$\Delta C = \Delta A / E$$

Where, $\Delta C$ was change in the concentration of NADPH, $\Delta A$ was change in absorbance, and E was extinction coefficient of NADPH (E340 nm=6.22 $mM^{-1} \cdot cm^{-1}$). FAS activity was expressed as n mol NADPH oxidized/min/mg protein.

Figure 6:
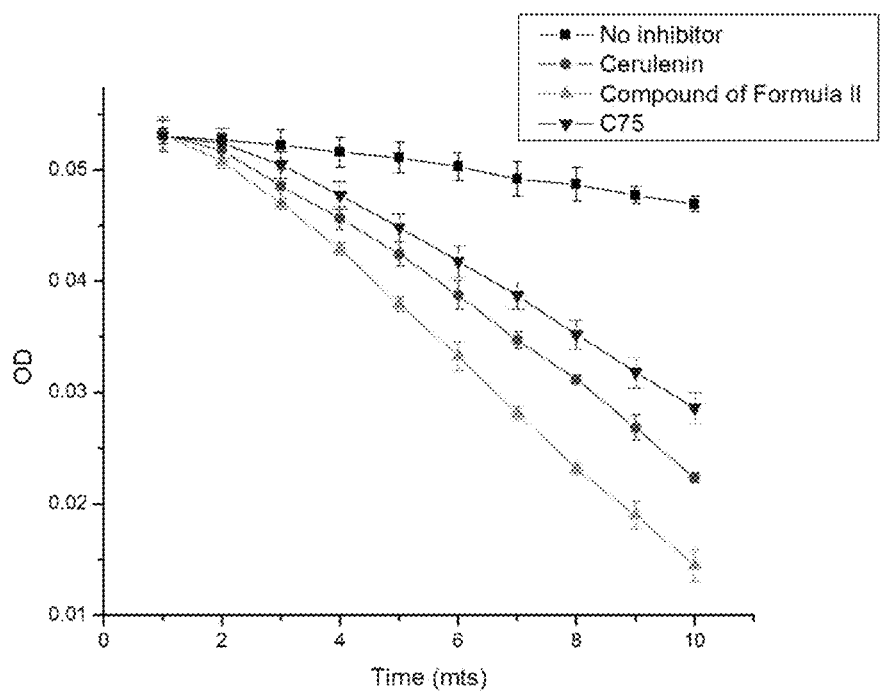
FIG. 6 illustrates results of assay for inhibition of bacterial FAS II enzyme by compound of Formula II
Figure 7:
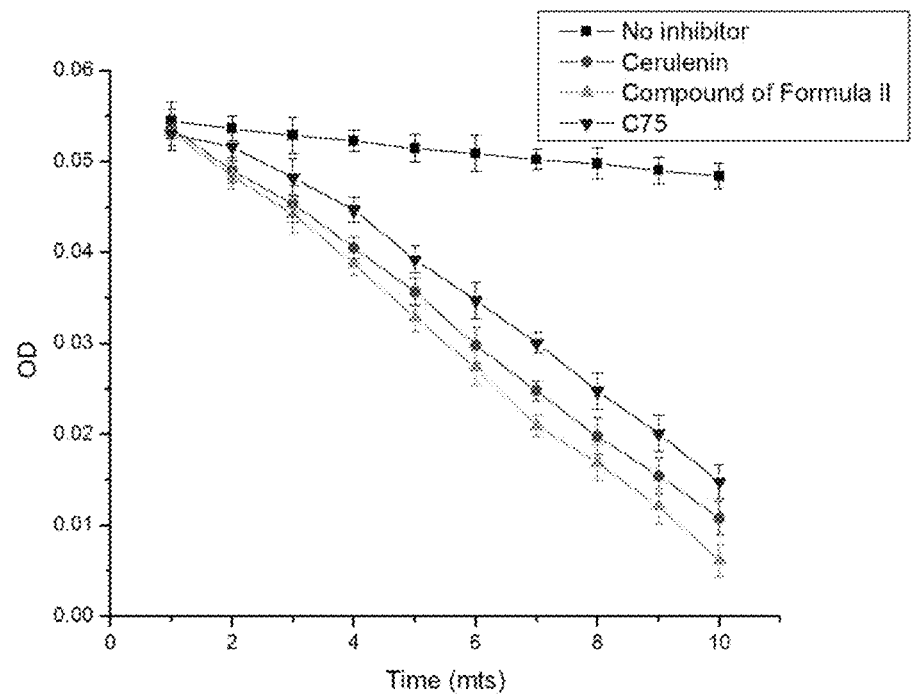
FIG. 7 illustrates results of assay for inhibition of bovine FAS I enzyme by compound of Formula II

Assay using partially purified enzyme from Bacillus subtilis was also performed to verify the FAS II inhibitory activity of compound of Formula II. At lower concentrations, compound of Formula II showed results comparable with Cerulenin and C75 and higher inhibition at higher concentration of compound of Formula II. The graph was plotted with change in concentration of NADP to NADPH against time. Each point in graph was the concentration of NADPH measured on a spectrophotometer at 340 nm (FIGS. 6 and 7 for FAS II and FAS I respectively).

TABLE 5

FAS inhibition activity of compound of Formula II vis-a-vis Cerulenin and C75 taken as standard inhibitors FAS I assay compared with known inhibitors

|  | Control | Cerulenin | Compound of Formula II | C75 |
| --- | --- | --- | --- | --- |
| Average ΔC | 0.051383 | 0.032476 | 0.030064 | 0.036125 |
| Inhibition compared to control |  | 36.49% | 41.49% | 29.60% |

FAS II assay compared with known inhibitors

|  | Control | Cerulenin | Compound of Formula II | C75 |
| --- | --- | --- | --- | --- |
| Average ΔC | 0.05037 | 0.03955 | 0.034984 | 0.042476 |
| Inhibition compared to control |  | 21.48% | 30.54% | 15.67% |

Example 5: Evaluation of ADME and Docking Studies

ADME Prediction

In a drug design point of view the ADME (absorption, distribution, metabolism, and excretion) properties of the compound of Formula II compared to the standard, Cerulenin and C75 was predicted using the Schrödinger suite's Qikprop module (QikProp, version 3.5, Schrödinger, LLC, New York,). Also, Qikprop can predict any possible drug leads by comparing the compound scaffolds with known database and analyzing similarity within a class of compounds (Schrödinger Release 2015: QikProp, Schrödinger, LLC, New York, N.Y., 2016.). Table 6 demonstrates that the Compound of Formula II exhibits values which fall well within the acceptable ranges for the ADME parameters as tested.

TABLE 6

ADME predictions of compound of Formula II vis-a-vis Cerulenin and C75 predicted using QikProp module of Schrodinger suit.

| Compound ID | #stars[a] | #rotor[b] | SASA[c] (Å) | Donor HB[d] | Accept HB[e] | QPlogPo/w[f] | QPlogKp[g] | PSA[h] (Å) |
| --- | --- | --- | --- | --- | --- | --- | --- | --- |
| Compound of Formula II | 0 | 10 | 726.16 | 5 | 7 | 1.882 | −5.27 | 106.23 |
| Cerulenin | 0 | 7 | 223.27 | 1 | 5 | 0.697 | −3.59 | 90.39 |
| C75 | 0 | 9 | 254.32 | 1 | 5 | 2.616 | −3.22 | 87.84 |

Recommended ranges:
[a]Number of descriptor values fall outside values of 95% known drugs: 0 to 5
[b]Number of rotatable bonds: 0-15
[c]Total solvent accessible surface area (SASA) in square angstroms: 300 to 1000
[d]Number of hydrogen-bond donors: 0 to 6
[e]Number of hydrogen-bond acceptors: 2 to 20
[f]Predicted octanol/water partition coefficient: −2 to 6.5
[g]Predicted skin permeability: −8.0 to −1.0
[h]van der Waals surface area of polar nitrogen and oxygen atoms and carbonyl carbon atoms: 7-200

Molecular Docking Studies

Molecular docking studies were carried out to explain the possible binding mode of the purified compound to FAS. Since the structure of the purified compound of Formula II was similar to Cerulenin, crystal structure with protein data bank (PDB) structure no. 4LS7 was selected as receptor which is of *Bacillus subtilis* FAS II beta-ketoacyl-ACP synthase II (FabF) domain with non-covalently bonded Cerulenin. Similarly, for studying the interactions of the ligand with mammalian FAS-I, PDB structure no. 3HHD (Pappenberger et al, 2010) consisting of human FAS-I's KS-MAT domain was taken as a framework. Prior to the docking studies, the receptor structure was prepared by deleting the crystallographic water molecules and adding hydrogen to polar atoms. Later, the disulphide bond lengths were corrected and a minimization was performed by applying a RMSD cut off 0.30 Å using a force field OPLS 2001. In PDB structure no. 4LS7 (Trajtenberg et al, 2014), Cerulenin at the active site was taken as reference and grid was generated with 15×15×15 Å volume surrounding the ligand. In case of PDB structure no. 3HHD, according to Wettstein-Knowles et al. (2006), active site residues CYS161, HIS331 and HIS293 play crucial roles in FAS I's activity, hence these residues were taken as the center and a grid was generated with a box dimensions of 15×15×15 Å. Docking simulation was performed using extra precision (XP) docking method implemented in Schrodinger version 9.4.0. (Friesner et al, 2006).

Calculation of Binding Free Energies

The docked poses with highest glide score were selected and binding free energies for the protein-ligand complex was calculated using Prime MM-GBSA. Prime MM-GBSA generates energy properties for the ligand, the receptor, and complex structure along with energy differences relating to strain and binding. Prime calculates the binding free energy using the equation:

$$\Delta G \text{ (bind)} = E\_\text{complex (minimized)} - (E\_\text{ligand (minimized)} + E\_\text{receptor (minimized)})$$

Inference

Figure 8:
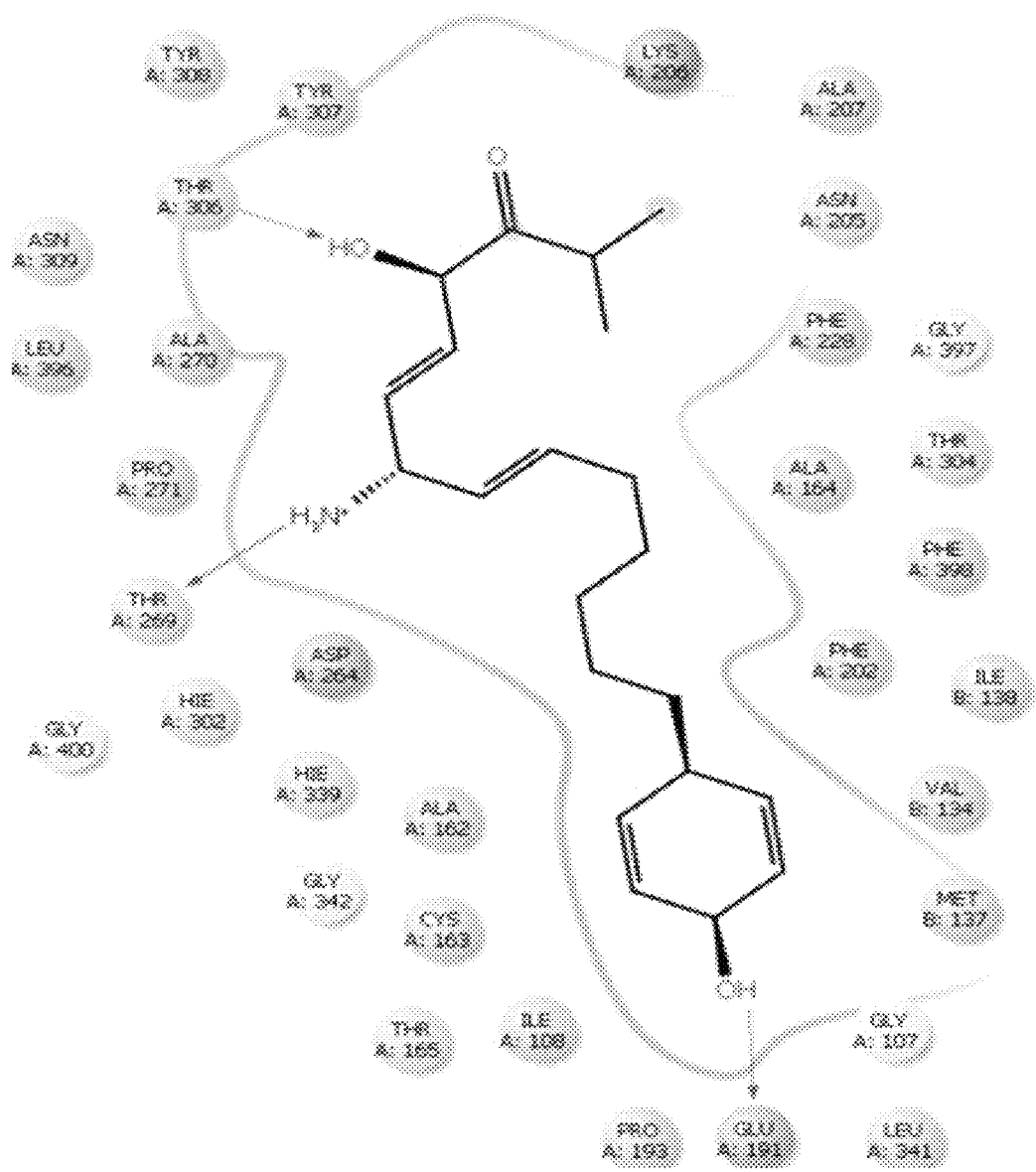
FIG. 8 illustrates compound of Formula II at active site of *Bacillus subtilis* FAS II β-ketoacyl-ACP synthase II
Figure 9:
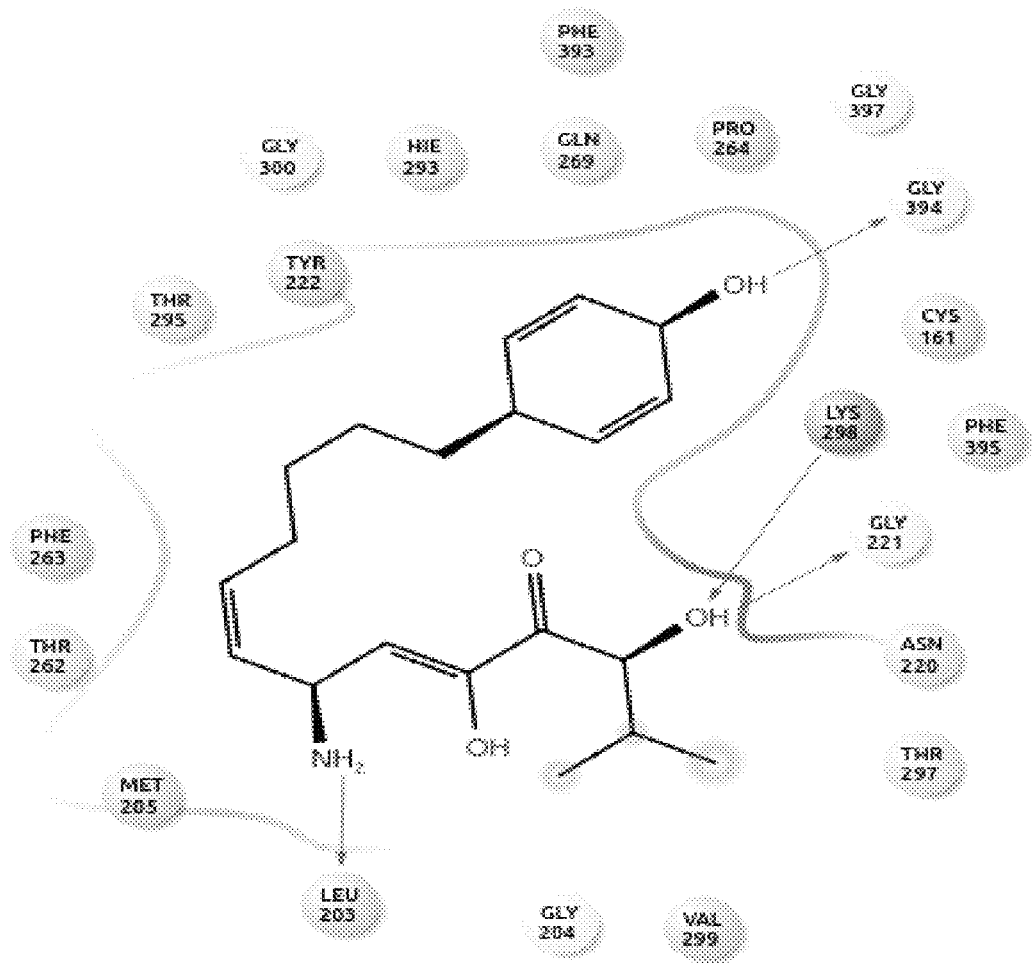
FIG. 9 illustrates compound of Formula II at active site of human FAS I KS-MAT domain

Binding result was interpreted based on the score obtained in docking studies as well as the theoretical binding energies calculated from the docked poses. Possible amino acid residues involved in binding and the type of interactions made by compound of Formula II with active site residues are shown in FIG. 8 for FAS II and in FIG. 9 in the case of FAS I. Table 7 and 9 for FAS II and FAS I respectively, indicate that the glide score as well as the theoretically calculated binding energy was better for compound of Formula II compared to that of both the other standard inhibitors. Glide score was calculated based on different parameters of ligand-protein interaction and it represented the overall affinity of ligand-protein binding. MMGBSA method was used to determine simulated binding free energy of ligand-protein interaction and more negative values represented tighter binders. Parameters like number of H-bonds between ligand atoms and active site residues, ligand interaction with number of hydrophobic residues and the total number of van der Waals contacts involved in ligand binding indicated the affinity and strength of ligand enzyme interactions. Table 8 and 10 give a comparison of total number of these parameters with respect to compound of Formula II and other two FAS inhibitors. It can be clearly seen that compound of Formula II has good interaction with both FAS II and FAS I enzymes when compared to other known inhibitors.

TABLE 7

Comparison of docking of Compound of Formula II, Cerulenin and C75 against Bacillus FAS II

| Compound | XP Glide Score (kcal/mol) | MMGBSA dG Bind (kcal/mol) |
|---|---|---|
| Compound of Formula II | −8.612 | −54.679 |
| Cerulenin | −7.589 | −48.109 |
| C75 | −5.040 | −30.549 |

TABLE 8

Number of interactions at 5 Å distance from active site with docked ligands in Bacillus beta-ketoacyl-ACP synthase II domain

| Compound | Number of Hydrogen bonds | Number of Hydrophobic residues at 5 Å distance | Number of van der Waals interactions |
|---|---|---|---|
| Compound of Formula II | 3 | 18 | 465 |
| Cerulenin | 2 | 17 | 347 |
| C75 | 3 | 13 | 341 |

TABLE 9

Comparison of docking of Compound of Formula II, Cerulenin and C75 against human FAS I

| Compound | XP Glide Score (kcal/mol) | MMGBSA dG Bind (kcal/mol) |
|---|---|---|
| Compound of Formula II | −5.093 | −43.936 |
| Cerulenin | −4.850 | −39.420 |
| C75 | −3.900 | −26.489 |

TABLE 10

Number of interactions at 5 Å distance from active site with docked ligands in human FAS IKS-MAT di-domain

| Compound | Number of Hydrogen bonds | Number of Hydrophobic residues at 5 Å distance | Number of van der Waals interactions |
|---|---|---|---|
| Compound of Formula II | 4 | 9 | 632 |
| Cerulenin | 3 | 8 | 363 |
| C75 | 1 | 8 | 454 |

The above analyses convincingly demonstrate that compound of Formula II is a better inhibitor of human and bacterial or eukaryotic and prokaryotic FAS enzymes in comparison to the inhibitors used currently as drugs.

We claim:

1. A compound of (3S,5Z,7S,8Z)-7-amino-3,5-dihydroxy-2-methyl-13-[(1s,4s)-4-hydroxycyclohexa-2,5-dien-1-yl]trideca-5,8-dien-4-one represented by Formula II:

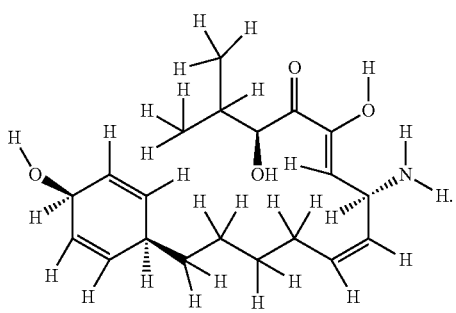

Formula II

2. The compound as claimed in claim 1, wherein the compound has a $^1$H and $^{13}$C NMR spectra with signals at δH 7.26 correlated with δC 67.62; δH at 2.46 to 2.62 and δC at 29.64; δH at 1.25 to 1.67; and 5.23 to 5.27.

3. A process for preparing the compound of the formula II as claimed in claim 1, comprising the steps of:
   a. collecting cyanobacterial biomass by scrapping off the cyanobacteria from semi submerged rock pits and washing with water;
   b. squeezing and grinding the biomass with ethanol to obtain a fine paste of the biomass;
   c. drying and solidifying the paste obtained in step (b) by spreading a thin layer of the paste;
   d. grinding the solidified paste obtained in step (c) into a powder;
   e. defatting the biomass powder obtained in step (d) using hexane;
   f. extracting the defatted powder obtained in step (e) using soxhlet at 60° C. to 70° C. for 6 to 8 hours using chloroform to obtain a pale white precipitate;
   g. concentrating the extract obtained in step (f) to $\frac{1}{5}^{th}$ of its original volume using a rotary vacuum evaporator operated at 145 rpm-155 rpm/and at 35° C.-45° C.;
   h. precipitating the concentrated extract obtained in step (g) using methanol and re-dissolving in chloroform;
   i. repeating step (h) 3 to 4 times or until precipitate of pale white color are obtained;
   j. purifying the precipitate obtained in step (i) using silica gel column chromatography carried out using ethyl acetate, dichloromethane and methanol as solvents for gradient elution and wherein elution is initiated with 100% ethyl acetate followed by attaining 100% dichloromethane in the middle and finally using 100% methanol in the last stage;
   k. purifying the compound obtained in step (j) using a vacuum liquid chromatography using 100% dichloromethane to 100% methanol for elution; and
   l. purifying the compound obtained in step (k) using a reverse phase High Pressure Liquid Chromatographic (R-HPLC) with a gradient elution using acetonitrile to water at a constant flow rate of 0.2 mL/min with a constant column temperature of 30° C.

4. The process as claimed in claim 3, wherein the collected cyanobacterial biomass is processed within 1-2 hours.

5. The process as claimed in claim 3, wherein the extraction of defatted powder in step (f) is carried out at 65° C.

6. The process as claimed in claim 3, wherein the concentration of extract in step (g) is carried out using a rotary vacuum evaporator operated at 150 rpm at 40° C.

7. A pharmaceutical composition produced by the process as claimed in claim 3, the pharmaceutical composition comprising said compound.

8. The pharmaceutical composition as claimed in claim 7, further comprising pharmaceutically acceptable excipients, diluents, or additives.

9. A pharmaceutical composition produced by the process as claimed in claim 5, the pharmaceutical composition comprising said compound.

10. A pharmaceutical composition produced by the process as claimed in claim 6, the pharmaceutical composition comprising said compound.

* * * * *